United States Patent
Itou

(10) Patent No.: US 7,637,875 B2
(45) Date of Patent: Dec. 29, 2009

(54) GUIDE WIRE

(75) Inventor: Yutaka Itou, Fujinomiya (JP)

(73) Assignee: Terumo Kabushiki Kaisha, Shibuya-Ku, Tokyo (JP)

(*) Notice: Subject to any disclaimer, the term of this patent is extended or adjusted under 35 U.S.C. 154(b) by 0 days.

(21) Appl. No.: 11/902,862

(22) Filed: Sep. 26, 2007

(65) Prior Publication Data

US 2008/0161726 A1    Jul. 3, 2008

Related U.S. Application Data

(60) Provisional application No. 60/878,660, filed on Jan. 5, 2007.

(30) Foreign Application Priority Data

Dec. 28, 2006    (JP) .............................. 2006-356643

(51) Int. Cl.
*A61M 25/00* (2006.01)
*A61M 5/178* (2006.01)

(52) U.S. Cl. .................... 600/585; 600/434; 604/164.13

(58) Field of Classification Search ................. 600/585, 600/434; 604/164.13
See application file for complete search history.

(56) References Cited

U.S. PATENT DOCUMENTS

| | | |
|---|---|---|
| 4,925,445 A | 5/1990 | Sakamoto et al. |
| 5,069,226 A | 12/1991 | Yamauchi et al. |
| 5,238,004 A | 8/1993 | Sahatjian et al. |
| 5,269,759 A | 12/1993 | Hernandez et al. |
| 5,368,049 A | 11/1994 | Raman et al. |
| 5,402,799 A | 4/1995 | Colon et al. |
| 5,411,476 A | 5/1995 | Abrams et al. |
| 5,452,726 A | 9/1995 | Burmeister et al. |
| 5,497,786 A | 3/1996 | Urick |
| 5,498,250 A | 3/1996 | Prather |
| 5,772,609 A | 6/1998 | Nguyen et al. |
| 5,797,857 A | 8/1998 | Obitsu |
| 5,876,356 A | 3/1999 | Viera et al. |
| 5,924,998 A | 7/1999 | Cornelius et al. |
| 5,951,494 A | 9/1999 | Wang et al. |
| 5,954,672 A * | 9/1999 | Schwager ................... 600/585 |
| 6,001,068 A | 12/1999 | Uchino et al. |
| RE36,628 E | 3/2000 | Sagae et al. |
| 6,093,157 A | 7/2000 | Chandrasekaran |
| 6,165,292 A | 12/2000 | Abrams et al. |
| 6,234,981 B1 | 5/2001 | Howland |
| 6,390,992 B1 | 5/2002 | Morris et al. |
| 6,520,923 B1 | 2/2003 | Jalisi |
| 6,679,853 B1 | 1/2004 | Jalisi |
| 2004/0030266 A1 | 2/2004 | Murayama et al. |
| 2004/0039308 A1 | 2/2004 | Murayama et al. |
| 2004/0039309 A1 | 2/2004 | Murayama et al. |
| 2005/0038359 A1* | 2/2005 | Aimi et al. .................. 600/585 |
| 2005/0152731 A1 | 7/2005 | Mishima et al. |

* cited by examiner

*Primary Examiner*—Max Hindenburg
*Assistant Examiner*—Emily M Lloyd
(74) *Attorney, Agent, or Firm*—Buchanan Ingersoll & Rooney PC

(57) ABSTRACT

A guide wire includes a wire body having a tapered portion disposed on a distal end portion thereof and having an outside diameter progressively reduced toward a distal end thereof. The guide wire also includes a coil having a first coil portion covering an outer circumferential surface of the tapered portion and a second coil portion disposed adjacent to a proximal end of the first coil portion and covering an outer circumferential surface of a constant-outside-diameter portion of the wire body. Initial tensile forces of the first coil portion are greater than initial tensile forces of the second coil portion.

16 Claims, 4 Drawing Sheets

GUIDE WIRE

This application claims the benefit of U.S. Provisional Application No. 60/878,660 filed on Jan. 5, 2007, the entire content of which is incorporated herein by reference. This application is also based on and claims priority to Japanese Application No. 2006-356643 filed on Dec. 28, 2006, the entire content of which is incorporated herein by reference.

TECHNOLOGICAL FIELD

The subject matter disclosed herein generally pertains to a guide wire.

BACKGROUND OF THE INVENTION

Guide wires are employed to guide catheters used in the treatment of, for instance, body regions that are difficult to operate on surgically, the treatment of body regions through minimally invasive surgery, and the inspection of blood vessels by cardiac angiography. For example, for performing PCI (Percutaneous Coronary Intervention) under X-ray radioscopy, the distal end of a guide wire is positioned to project from the distal end of a balloon catheter, and the guide wire as well as the balloon catheter are together inserted into the blood vessel up to a position near the constricted area of the coronary artery in question for guiding the distal end of the balloon catheter to a position near the constricted area.

One example of a guide wire used in the above treatment applications is disclosed in U.S. Pat. No. 5,797,857. The disclosed guide wire includes a flexible wire body (core), a coil (a metal coil for X-ray angiography) disposed in surrounding relation to the distal end of the wire body, and a covering layer (a covering member of synthetic resin, a hydrophilic lubricating layer) covering the outermost surfaces of the wire body and the coil.

When the guide wire disclosed in U.S. Pat. No. 5,797,857 is used to guide the catheter as described above, the following phenomena tend to occur depending on the state of the coronary artery such as the degree of curvature of the coronary artery.

If the guide wire is pushed in when the coil of the guide wire comes (is inserted) to a sharp bend of the coronary artery, for example, undue forces (tending to cause a plastic deformation) are liable to be applied to the coil. At this time, a turn of the wire of the coil rides onto an adjacent turn of the wire, tend to plastically deform the coil. Therefore, the coil will not recover its ordinary (normal) state, and the pushing force applied from the proximal end of the wire body will not be reliably transmitted to the distal end of the wire body, i.e., the guide wire pushing capability is greatly reduced.

Though the coil of the guide wire disclosed in U.S. Pat. No. 5,797,857 has a hydrophilic lubricating layer, a relatively large frictional resistance is developed between the hydrophilic lubricating layer and a sharp bend of the coronary artery, depending on the thickness of the guide wire when the coil of the guide wire comes (is inserted) to a sharp bend of the coronary artery. Therefore, the torque from the proximal end of the guide wire is not reliably transmitted through the coil to the distal end of the wire body, i.e., the torque transmitting capability is greatly reduced.

SUMMARY

A guide wire includes a wire body having a tapered portion disposed on a distal end portion thereof and having an outside diameter progressively reduced toward a distal end thereof. The guide wire includes a coil made of helically formed wire which includes a first coil portion covering an outer circumferential surface of the tapered portion and a second coil portion disposed adjacent to a proximal end of the first coil portion and covering an outer circumferential surface of a portion of the wire body which is closer to a proximal end thereof than the tapered portion. The adjacent turns of the wire of the first coil portion are held in contact with each other, and initial tensile forces developed for pushing the turns of the wire in the first wire portion against each other axially of the wire body in their free state are greater than initial tensile forces developed in the second coil portion.

Preferably, the portion of the wire body which is closer to the proximal end thereof than the tapered portion has an outside diameter substantially constant along a longitudinal direction of the wire body. The guide wire can be configured so that adjacent turns of the wire of the second coil portion are held in contact with each other. Alternatively, adjacent turns of the wire of the second coil portion can be spaced apart from each other.

The first coil portion preferably has a wire diameter which is the same as the wire diameter of the second coil portion, and preferably has an outside diameter which is the same as the outside diameter of the second coil portion. The first coil portion can also possess an inside diameter which is the same as the inside diameter of the second coil portion. The first coil portion and the second coil portion can be made of the same material or different materials.

The guide wire can be provided with fixing materials fixing the coil to the wire body at a plurality of locations, wherein the fixing materials are disposed at positions other than the boundary between the first coil portion and the second coil portion.

The wire of the first coil portion preferably has an angiographic portion. The wire forming the coil can be comprised of a first wire and a second wire, with the first wire comprising the first and second coil portions, and the second wire forming the angiographic portion and possessing a wire diameter greater than the wire diameter of the first wire. The second wire meshes with the first wire at a boundary between the distal end of the first wire and the proximal end of the second wire. The wire body can be configured to have a reduced diameter portion disposed on the distal end portion thereof and having an outside diameter progressively reduced toward a distal end thereof.

According to another aspect, a guide wire comprises a wire body having a tapered portion disposed on a distal end portion of the wire body, with the tapered portion of the wire body possessing an outside diameter that is progressively reduced toward a distal end of the tapered portion, and a coil disposed in covering relation to the outer circumferential surface of the distal end portion of the wire body, with the coil being comprised of at least one helically formed wire. The coil comprises a first coil portion covering an outer circumferential surface of the tapered portion and a second coil portion covering an outer circumferential surface of a portion of the wire body other than the tapered portion. The coil is preferably configured so that adjacent turns of the at least one wire of the first coil portion are in contact with each other, and initial tensile forces which push the adjacent turns of the at least one wire in the first coil portion against each other axially of the wire body in a free state are greater than the initial tensile forces in the second coil portion in the free state.

BRIEF DESCRIPTION OF THE DRAWING FIGURES

The above and other features and aspects disclosed herein will become more apparent from the following description when taken in conjunction with the accompanying drawing figures which are briefly described below.

DETAILED DESCRIPTION

Figure 1:
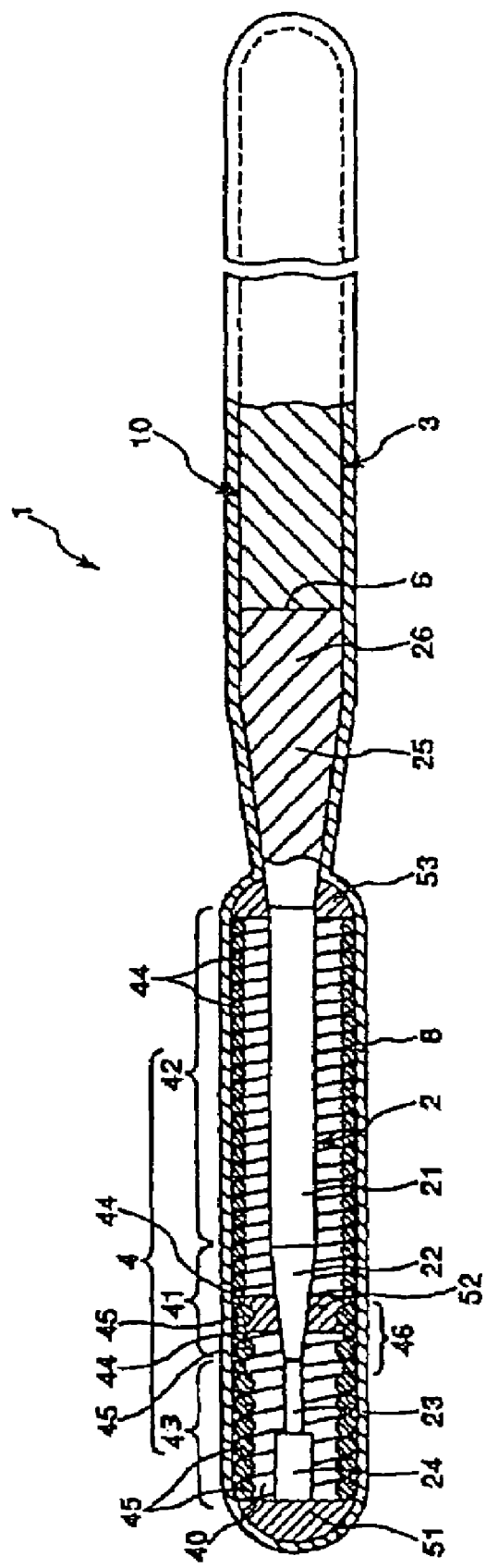
FIG. 1 is a side view, partially in longitudinal cross-section, of a guide wire according to a first embodiment disclosed herein.
Figure 2:
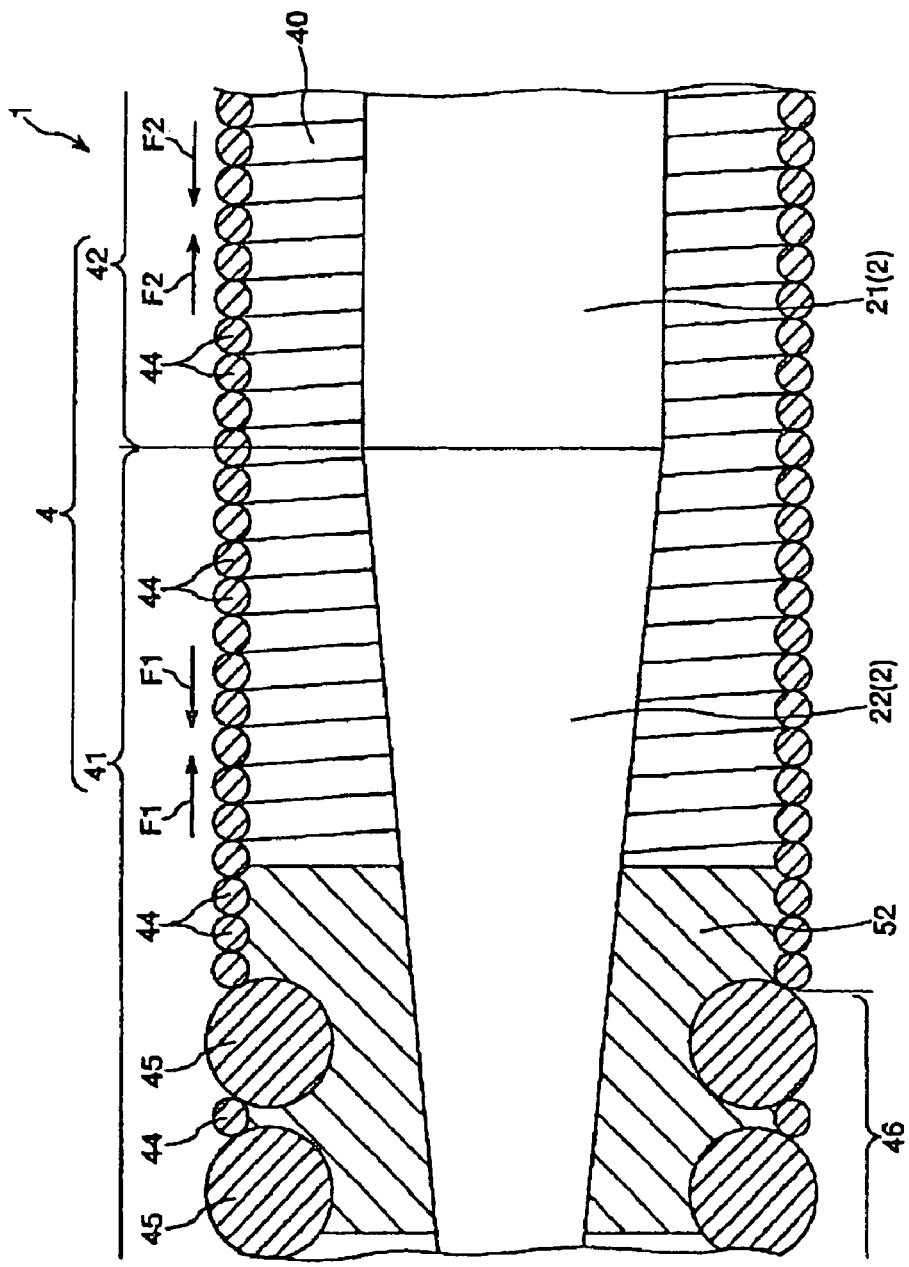
FIG. 2 is an enlarged detailed view of a tapered portion of the guide wire shown in FIG. 1.

FIGS. 1-2 illustrate a guide wire according to one embodiment. In the description that follows, the rightward end in FIGS. 1 and 2 (also FIG. 3) is referred to as the "proximal end" and the leftward end is referred to as the "distal end." For ease in understanding, FIGS. 1 and 2 (also FIG. 3) illustrate the guide wire at a reduced scale in its longitudinal direction, and at an exaggerated scale in its transverse direction so that the illustrated ratio between the longitudinal and transverse dimensions is different from the actual ratio. In FIG. 2 (also FIG. 3), a resin coating layer is omitted from illustration.

The guide wire 1 shown in FIG. 1 is a catheter guide wire configured to be inserted into the lumen of a catheter (including an endoscope). The guide wire 1 includes a wire body 10 comprised of a first wire 2 disposed on the distal end portion of the wire body 10 and a second wire 3 disposed on the proximal end portion of the wire body. The second wire 3 is joined (coupled) to the first wire 2, preferably by welding, and a helical coil 4 is disposed on the distal end portion (a portion near the distal end) of the wire body 10. The total length of the guide wire 1 is not limited to any value, but should preferably be in the range from about 200 to 5000 mm.

The first wire 2 is made of a wire material which is flexible or elastic. In the present embodiment, the first wire 2 includes a constant-outside-diameter portion 21 possessing a constant outside diameter (inclusive of substantially constant outside diameter) along its longitudinal extent, a smaller-diameter portion 23 positioned more closely to the distal end than the constant-outside-diameter portion 21 and possessing an outside diameter smaller than the constant-outside-diameter portion 21, a tapered portion 22 positioned between the constant-outside-diameter portion 21 and the smaller-diameter portion 23 and possessing an outside diameter progressively smaller toward the distal end, a flat plate portion 24 positioned on the distal end of the smaller-diameter portion 23 and shaped as a flat plate, a larger-diameter portion 26 positioned more closely to the proximal end than the constant-outside-diameter portion 21 and possessing an outside diameter greater than the constant-outside-diameter portion 21, and a tapered portion 25 positioned between the constant-outside-diameter portion 21 and the larger-diameter portion 26 and possessing an outside diameter progressively greater toward the proximal end. In the illustrated embodiment, the smaller-diameter portion 23 possesses a constant outer diameter (inclusive of substantially constant outer diameter). The flat plate portion 24, the smaller-diameter portion 23, the tapered portion 22, the constant-outside-diameter portion 21, the tapered portion 25, and the larger-diameter portion 26 are successively arranged in that order from the distal end of the first wire 2.

Since the smaller-diameter portion 23 and the constant-outside-diameter portion 21 are formed with the tapered portion 22 interposed therebetween, the rigidity (bending rigidity, torsional rigidity) of the first wire 2 is progressively reduced toward the distal end. As a result, the distal end portion of the guide wire 1 is well suited to passing through constricted portions and is flexible, so that the guide wire 1 has an increased ability to follow blood vessels or the like, is highly safe, and is inhibited from being bent over.

Furthermore, since the constant-outside-diameter portion 21 and the larger-diameter portion 26 are formed with the tapered portion 25 interposed therebetween, as with the tapered portion 22, the rigidity (bending rigidity, torsional rigidity) of the first wire 2 is progressively reduced toward the distal end.

The taper angle (the rate at which the outside diameter decreases) of the tapered portion 22 (also the tapered portion 25) may be constant along the longitudinal direction of the wire or may vary along the longitudinal direction of the wire. For example, the tapered portion may have a plurality of alternately repetitive regions where the taper angle (the rate at which the outside diameter decreases) is relatively large and relatively small.

The flat plate portion 24 is in the form of a flat plate (ribbon), and can be reshaped to a desired shape. In general, the distal end of the guide wire may be bent in advance (prior to use) to a desired shape by the doctor for shaping the distal end of the guide wire so that it can be relatively smoothly advanced through a blood vessel branch. Bending the distal end of the guide wire to a desired shape is referred to as reshaping. The flat plate portion 24 allows the guide wire 1 to be reshaped relatively easily and reliably to increase the operability of the guide wire 1 when it is inserted into a living body.

The constant-outside-diameter portion 21 and the larger-diameter portion 26 are constant in outside diameter along the longitudinal direction of the wire. The outside diameter of the constant-outside-diameter portion 21 is the same (inclusive of substantially the same) as the minimum outside diameter of the tapered portion 25 (e.g., the outside diameter of the tapered portion 25 at the distal end of the tapered portion 25), and the outside diameter of the larger-diameter portion 26 is the same (inclusive of substantially the same) as the maximum outside diameter of the tapered portion 25 (e.g., the outside diameter of the tapered portion 25 at the proximal end of the tapered portion 25).

The second wire 3 has its distal end joined (coupled) to the proximal end of the first wire 2 (the proximal end of the larger-diameter portion 26), preferably by welding. The second wire 3 is made of a wire material which is flexible or elastic.

The welding process by which the first wire 2 and the second wire 3 may be welded to each other is not limited to any particular welding processes. For example, the welding process may be friction welding, laser-beam spot welding, butt resistance welding such as upset welding, or the like. Butt resistance welding is preferable as it can achieve high bonding strength relatively easily.

In the present embodiment, the second wire 3 is constant in outside diameter (inclusive of substantially constant in outside diameter). The outside diameter of the second wire 3 is the same (inclusive of substantially the same) as the outside diameter of the larger-diameter portion 26 of the first wire 2.

Therefore, when the proximal end of the larger-diameter portion 26 of the first wire 2 and the distal end of the second wire 3 are joined to each other at a joint region, no step is produced on the outer circumferential surface at the joint region (welded region) 6 by any difference in outside diameter between the wires 2, 3, and so a continuous or smooth surface transition exists between the two wires 2, 3.

The average outside diameter of the first wire 2 is smaller than the average outside diameter of the second wire 3. Average outside diameter refers to the outside diameter obtained by measuring the outside diameter of the wire at five randomly chosen places and averaging the diameter obtained at the five locations. With the average outside diameter of the first wire 2 being smaller than the average outside diameter of the second wire 3, the guide wire 1 is relatively flexible at the first wire 2 on the distal end portion thereof, and is relatively highly rigid at the second wire 3 on the proximal end portion thereof. Consequently, the guide wire 1 has both flexibility at the distal end portion and excellent operability (pushing capability, torque transmission capability, etc.).

The material forming the first wire 2 and the material forming the second wire 3 are not limited to any particular materials. For example, each of the first wire 2 and the second wire 3 may be made of any of various metal materials including stainless steel (e.g., all SUS types such as SUS304, SUS303, SUS316, SUS316L, SUS316 J1, SUS316J1L, SUS405, SUS430, SUS434, SUS444, SUS429, SUS430F, SUS302), piano wire, cobalt-based alloy, pseudoelastic alloy (including superelastic alloy), etc. Of these metal materials, pseudoelastic alloy (including superelastic alloy) is particularly preferable, and superelastic alloy is more preferable.

The superelastic alloy is relatively pliable, has recoverability, and is less liable to remain bent when a bending force is applied. If the first wire 2 is made of superelastic alloy, the distal end portion of the guide wire 1 is sufficiently flexible and recoverable when it is bent, has an increased ability to follow blood vessels that are intricately curved and bent, and is of excellent operability. Furthermore, as the first wire 2 is less liable to remain bent due to its recoverability even when the first wire 2 is repeatedly curved and flexurally deformed, the first wire 2 is inhibited from having its operability lowered due to the tendency to remain bent as might otherwise occur during use of the guide wire 1.

The superelastic alloy includes those which exhibit different tensile stress vs. strain curves (i.e., the superelastic alloys which can be used here are not limited to superelastic alloys having a particular tensile stress vs. strain curve), those which have transformation points such As (austenite start temperature), Af (austenite finish temperature), Ms (martensite start temperature), Mf (martensite finish temperature), etc. measurable clearly or not, and those which are largely deformed (strained) under stresses and return to their original shape upon removal of the stresses.

Preferable compositions of the superelastic alloy include Ni—Ti-based alloy such as Ni-Ti alloy containing 49 to 52 atomic % of Ni, Cu—Zn alloy containing 38.5 to 41.5 weight % of Zn, Cu—Zn—X alloy (X represents at least one of Be, Si, Sn, Al, and Ga) containing 1 to 10 weight % of X, Ni—Al alloy containing 36 to 38 atomic % of Al, etc. Of these alloys, the Ni—Ti-based alloy is particularly preferable. The superelastic alloy, which is typified by the Ni—Ti-based alloy, is also excellent in its ability to adhere closely to a resin covering layer 8 to be described later.

The cobalt-based alloy in the form of a wire has a high modulus of elasticity and has an appropriate elastic limitation. Therefore, a wire made of cobalt-based alloy has excellent torque transmitting capability and is less susceptible to problems such as buckling. Any cobalt-based alloys may be used insofar as they contain Co as a component. However, cobalt-based alloys which contain Co as a chief component (i.e., cobalt-based alloys containing Co at the highest weight ratio among the elements of the alloy) are preferable, and Co—Ni—Cr-based alloy is more preferable. The alloys of this composition exhibits the above advantages quite well. The wire formed of the alloys of this composition has a relatively high modulus of elasticity, can be cold-formed even if they have a high elastic limitation, and can be reduced in diameter while sufficiently preventing themselves from buckling because of the high elastic limitation. Also, the wire of these alloys is flexible and rigid enough to be inserted into a given region.

The first wire 2 and the second wire 3 may be made of different materials, or may be made of the same metal material or metal materials of the same kind (containing the same main metal in the alloy composition). The first wire 2 and the second wire 3 thus constructed provide a higher bonding strength at the joint (welded region) 6, are not liable to be torn apart even if the outside diameter of the joint 6 is small, and exhibit excellent torque transmitting capability.

If the first wire 2 and the second wire 3 are made of different materials, the first wire 2 should preferably be made of a superelastic alloy as referred to above, and more preferably should be made of a Ni—Ti-based alloy, and the second wire 3 should preferably be made of stainless steel.

Though the first wire 2 and the second wire 3 have been described above as being joined to each other, they may be replaced with a single wire free of joints. The single wire may be made of the materials described above, and should preferably be made of stainless steel, cobalt-based alloy, or superelastic alloy.

The coil 4 is disposed around the distal end portion of the wire body 10 in covering relation thereto. The coil 4 thus placed on the distal end portion of the wire body 10 reduces the area of contact of the wire body 10 with the inner wall of the catheter and the living body surface, resulting in reduced sliding resistance. As a result, the operability of the guide wire 1 is increased.

As shown in FIG. 1, the wire body 10 is positioned centrally inside the coil 4. The wire body 10 is positioned so that the outer surface of the wire body 10 is spaced from and not in contact with the inner surface of the coil 4, with a gap 40 defined between the inner surface of the coil 4 and the outer surface of the wire body 10.

The coil 4 can be divided into three portions. Specifically, the coil 4 can be divided into a first coil portion 41 covering the outer circumferential surface of the tapered portion 22 of the wire body 10, a second coil portion 42 covering the outer circumferential surface of the constant-outside-diameter portion 21, and a third coil portion 43 covering the outer circumferential surface of the flat plate 24 and the smaller-diameter portion 23. The third coil portion 43, the first coil portion 41, and the second coil portion 42 are successively disposed (adjacent to each other) in that order from the tip end of the coil 4.

The coil 4 includes a section where a wire (first wire) 44 having a circular cross-sectional area is helically wound and a section which is disposed more closely to the distal end than the section where the wire 44 is helicall wound, and where a wire (second wire) 45 having a circular cross-sectional area is helically wound. The section where the wire 44 is helically wound and the section where the wire 45 is helically wound mesh with each other across their boundary (i.e., in a longitudinally extending overlapping region of the two wires 44, 45). The region where the wires 44, 45 helically mesh with each other is referred to as a "biting region 46". The biting region 46 may also be referred to as a coupling region (wire coupling region) where the wires 44, 45 are coupled to each other.

With the inclusion of the biting region 46, the bonding strength between the helical wire 44 and the helical wire 45 is sufficiently maintained by filling the space between the overlapping portions of the wires 44, 45 and the first wire 2 with a fixing material 52.

The third coil portion 43 is comprised of the wire 45, the second coil portion 42 is comprised of the wire 44, and the first coil portion 41 is comprised of the wires 44, 45.

The wires 44, 45 may be made of either a metal material or a resin material. The wires 44, 45 may be made of the same material or different materials. In the present embodiment, the wires 44, 45 are made of different materials, respectively. According to a preferred example, the wire 45 is made of an X-ray-impermeable material (e.g., Pt—Ni alloy), and the wire 44 is made of a material that is relatively permeable to X-rays (e.g., stainless steel). The wires 44, 45 thus made of these materials allow the tip end portion of the guide wire 1 to be compatible with X-ray angiography, so that the tip end portion of the guide wire 1 can be inserted into a living body while its position is being confirmed under X-ray angiography. The wire 45 thus constitutes an angiographic wire, and so the first coil portion 41 includes an angiographic portion defined by at least the portion of the wire 45 in the first coil portion 41.

If the wire 45 is made of Pt—Ni alloy and the wire 44 of stainless steel, the diameter of the wire 45 is preferably set to a value greater than the diameter of the wire 44 (see FIGS. 1 and 2). Thus, under X-ray radioscopy, the wire 45 positioned in the tip end portion of the coil 4 is better highlighted (more easily visually perceived) than the wire 44 that is positioned more closely to the proximal end than the wire 45. Therefore, the position of the foremost end portion (portion corresponding to the wire 45) of the guide wire 1 can be confirmed.

As described above, the first coil portion 41 is constructed of the wires 44, 45. That is, the first coil portion 41 includes a distal portion of the wire 44 and a proximal portion of the wire 45, including the region where the wires 44, 45 mesh with one another.

As shown in FIG. 2 (also FIG. 1), adjacent turns of the wire 44 are held in contact with each other in the first coil portion 41, except at the distal end of the wire 44 where the wire 44 is meshed with the wire 45. Initial tensile forces F1 are developed in the wire 44 for pushing the turns of the wire 44 against each other axially of the wire body 10 in their free state. The term "free state" means a state in which no external forces are applied. The term "initial tensile forces" generally refers to "compressive forces" of the coil (the first coil portion 41).

The process of manufacturing the first coil portion 41 to develop the initial tensile forces F1 in the free state is not limited to any processes. For example, the process to be described below may be employed. This process is described below with reference to FIG. 4.

A bobbin 90 around which is wound the wire 44 of stainless steel is prepared. The end portion (free end portion) of the wire 44 is unreeled from the bobbin 90 and is wound around a jig 80 (rod) in the direction indicated by the arrow A in FIG. 4. The jig 80 possesses a round cross-section. The wire 44 is helically wound around the jig 80 as the jig 80 progressively moves in the direction indicated by the arrow B.

Figure 4:
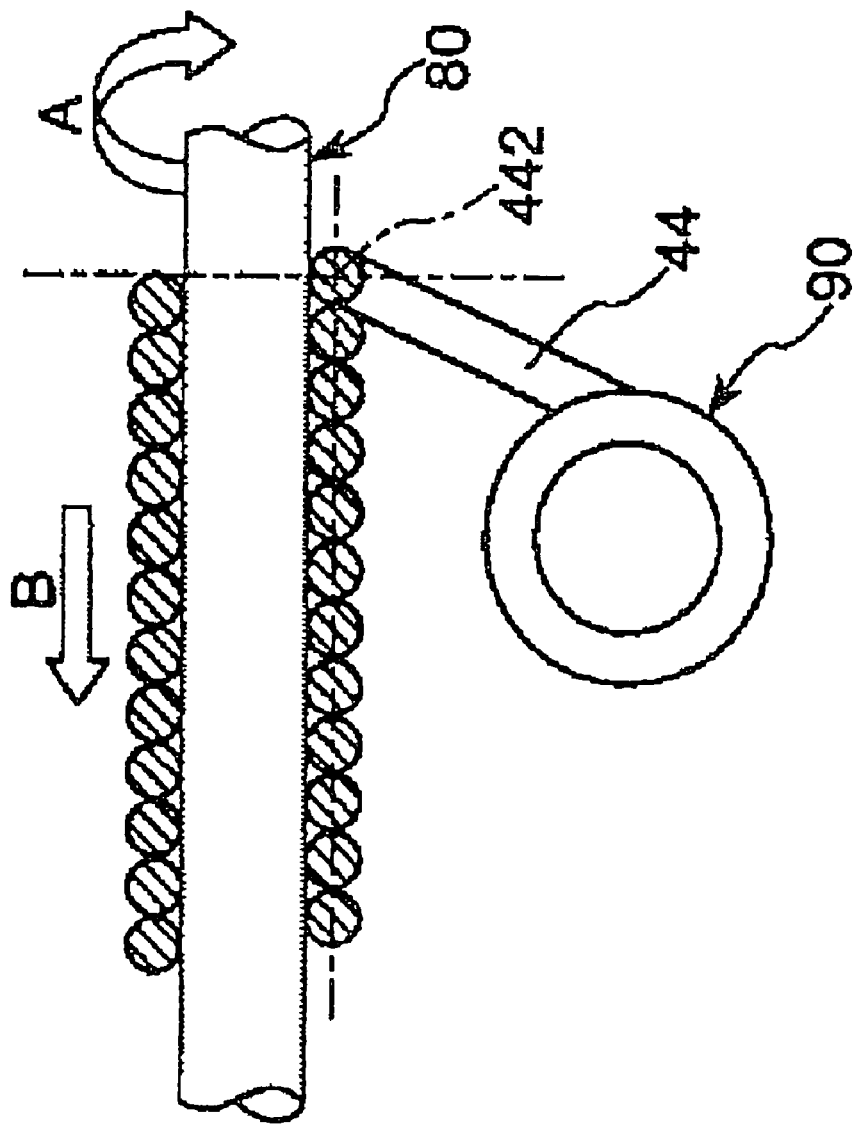
FIG. 4 is a somewhat schematic illustration of a method of manufacturing a first coil of the coil used in the guide wire shown in FIG. 1.

The wire 44 is supplied to the jig 80 from an area that is leftward in FIG. 4 of a winding position 442. As illustrated in FIG. 4, the bobbin 90 from which the wire 44 is unwound is always located to the left of the winding position 442 (i.e., the bobbin 90 is positioned in the direction B relative to the winding position 442). In this manner, it is possible to obtain the first coil portion 41 in which the initial tensile forces F1 are developed in the free state.

The first coil portion 41 produced in the foregoing manner may be heat-treated. If the first coil portion 41 is excessively heat-treated, then the initial tensile forces F1 may possibly be suppressed. However, the first coil portion 41 can appropriately be heat-treated to finely adjust the initial tensile forces F1. If the initial tensile forces F1 are to be partly changed, the initial tensile forces F1 can be reduced (suppressed), for example, by heat-treating the first coil portion 41.

As shown in FIG. 2, adjacent turns of the wire 44 are held in contact with each other in the second coil portion 42 in a manner similar to the first coil portion 41. Initial tensile forces F2 may be developed for pushing the turns of the wire 44 against each other axially of the wire body 10 in their free state, or may not be developed (the initial tensile forces F2=0).

The wire 44 of the guide wire 1 is constructed so that the initial tensile forces F1 in the free state of the wire in the first coil portion 41 compared to the initial tensile forces F2 in the free state of the wire in the second coil portion 42 are such that the initial tensile forces F1>the initial tensile forces F2. This relationship between the magnitudes of the initial tensile forces F1 and the initial tensile forces F2 can be achieved by changing the position where the wire 44 is supplied from the area that is leftward in FIG. 4 of the winding position 442 and the magnitudes of the forces (i.e., the magnitude of the tension between the bobbin 90 and the winding position 442).

When the guide wire 1 in the living body is manipulated, i.e., when it is pushed in, a turn of the wire 44 is more liable to ride onto an adjacent turn in the first coil portion 41 covering the tapered portion 22 (i.e., the portion where the gap 40 is relatively large or wide) than in the second coil portion 42. However, since the initial tensile forces F1 of the first coil portion 41 are greater than the initial tensile forces F2 of the second coil portion 42, the coupling forces between the turns of the wire 44 of the first coil portion 41 are greater than the forces tending to cause turns of the wire 44 to ride onto adjacent turns of the wire 44 of the first coil portion. Accordingly, turns of the wire 44 are generally inhibited or prevented from riding onto an adjacent turn. The guide wire 1 can thus be used in a desired manner in which the pushing forces are relatively reliably transmitted to the distal end of the guide wire 1.

As described above, the first coil portion 41 and the second coil portion 42 are made, or composed, of the same helically coiled wire 44. Therefore, as shown in FIG. 2, the wire diameter of the proximal end portion (partial) of the first coil portion 41 and the wire diameter of the second coil portion 42 are the same as each other. The outside diameter of the proximal end portion of the first coil portion 41 and the outside diameter of the second coil portion 42 are also the same as each other. Further, the inside diameter of the proximal end portion of the first coil portion 41 and the inside diameter of the second coil portion 42 are the same as each other.

Since the wire diameters are the same as each other, the forces borne by the first coil portion 41 and the second coil portion 42 can be relatively uniformly distributed. Therefore, when the guide wire 1 is manipulated, the first coil portion 41 and the second coil portion 42 are relatively reliably prevented from being unduly deformed, e.g., kinked. As the first coil portion 41 and the second coil portion 42 can be continuously wound at the same diameter, the coil 4 can be manufactured at a relatively low cost and the manufacturing process is simplified. If the wire diameter changes somewhere along the length of the coil 4, a stress concentration can occur in the area where the wire diameter changes. The same wire diameter, however, is advantageous in that it does not result in the stress concentrations which would otherwise result from a change in diameter.

Also, as the outside diameters are the same as each other, the resistance to the insertion of the guide wire 1 into a catheter or a living body is reduced.

The ratio F1/F2 between the initial tensile forces F1 and the initial tensile forces F2 is not limited to any particular value. However, the ratio F1/F2 should preferably be in the range from 1.1 to 20, more preferably in the range from 2 to 10.

By reducing gradually and distally the initial tensile forces of the proximal end portion of the first coil portion 41, stresses can be distributed between the first coil portion 41 and the second coil portion 42.

The first coil portion 41 and the second coil portion 42 of the guide wire 1 (the coil 4) are made of the same wire 44, i.e., stainless steel, as described above. In the present embodiment, the first coil portion 41 and the second coil portion 42 are not limited to the above material, but may be made of other materials.

If the first coil portion 41 and the second coil portion 42 are made of the same material, the kinds of materials used is reduced, and the cost at which the guide wire 1 (the coil 4) is manufactured is reduced. If the first coil portion 41 and the second coil portion 42 are made of different materials, materials suitable for forming the first coil portion 41 and the second coil portion 42 can be used.

As shown in FIG. 1, the coil 4 is fixed to the wire body 10 at three locations. Specifically, the distal end of the third coil portion 43 is fixed to the distal end of the first wire 2 by a fixing material (fixing member) 51. The proximal end of the second coil portion 42 is fixed to an intermediate portion of the first wire 2 (near the boundary between the constant-outside-diameter portion 21 and the tapered portion 25) by a fixing material (fixing member) 53. The biting region 46 is fixed to the tapered portion 22 of the first wire 2 by the fixing material (fixing member) 52. By thus fixing the coil 4 at the above locations, the first coil portion 41, the second coil portion 42, and the third coil portion 43 can be reliably fixed in position without impairing the flexibility of the distal end portion of the guide wire 1 (where the coil 4 is present).

The fixing materials 51, 52, 53 are made of solder (brazing material). However, the fixing materials 51, 52, 53 are not limited to solder, but may be an adhesive. The manner by which the coil 4 is fixed to the wire body 10 is not limited to the fixing materials, but also can be achieved by welding, for example. In order to prevent damage to the inner wall of a lumen such as a blood vessel or the like, the distal end surface of the fixing material 51 should preferably be round.

Though the fixing material 52 is disposed in the biting region 46, the fixing material 52 is not limited to such a position, but may be disposed anywhere in the coil 4 except the boundary between the first coil portion 41 and the second coil portion 42. If the fixing material 52 is placed at the boundary between the first coil portion 41 and the second coil portion 42, then depending on the manner in which the boundary between the first coil portion 41 and the second coil portion 42 is formed, the rigidity may not vary sufficiently gradually from the second coil portion 42 to the first coil portion 41.

As shown in FIG. 1, the entire outer surface of the guide wire 1, along its full longitudinal extent, is covered with a resin covering layer 8. The resin covering layer 8 may be formed for various purposes. For example, the resin covering layer 8 serves to reduce the friction (frictional resistance) of the guide wire 1 for increased slidability to increase the operability of the guide wire 1.

In order to reduce the friction (frictional resistance) of the guide wire 1, the resin covering layer 8 should preferably be made of a material capable of reducing friction as described below. The frictional resistance (sliding resistance) between the guide wire 1 and the inner wall of the catheter that is used with the guide wire 1 is reduced to increase slidability, allowing the guide wire 1 to be well operated in the catheter. Moreover, since the sliding resistance to the guide wire 1 is reduced, when the guide wire 1 is moved and/or turned in the catheter, the guide wire 1 is relatively reliably prevented from being kinked or twisted, particularly in the vicinity of the joint region 6.

Material capable of reducing friction may be polyolefin such as polyethylene, polypropylene, or the like, polyvinyl chloride, polyester (PET, PBT, or the like), polyamide, polyimide, polyurethane, polystyrene, polycarbonate, silicone resin, fluororesin (PTFE, ETFE, or the like), or a composite material thereof.

The resin covering layer 8 may be provided for the purpose of increasing safety upon insertion of the guide wire 1 into a blood vessel or the like. To serve the purpose, the resin covering layer 8 should preferably be made of a highly pliable material (soft material, elastic material).

The highly pliable material may be polyolefin such as polyethylene, polypropylene, or the like, polyvinyl chloride, polyester (PET, PBT, or the like), polyamide, polyimide, polyurethane, polystyrene, silicone resin, thermoplastic elastomer such as polyurethane elastomer, polyester elastomer, polyamide elastomer, or the like, any of various rubber materials such as latex rubber, silicone rubber, or the like, or a composite material comprising two or more of the above materials in combination.

The resin covering layer 8 may be a single layer or a laminated body of two ore more layers. Though it is preferable to apply the covering layer 8 along the entire longitudinal extent of the guide wire, it is recognized that instances may arise where it is desirable to apply the covering layer to only a portion of the longitudinal extent of the guide wire.

At least the outer surface of the distal end portion of the guide wire 1 should preferably be coated with a hydrophilic material. The hydrophilic material is wetted to provide lubrication for reducing friction (sliding resistance) of the guide wire 1 and thereby achieve increased slidability. Therefore, the operability of the guide wire 1 is increased.

The hydrophilic material may be cellulose-based polymeric material, polyethylene-oxide-based polymeric material, maleic-anhydride-based polymeric material (e.g., maleic anhydride copolymer such as methylvinylether-maleic anhydride copolymer), acrylamide-based polymeric material (e.g., polyacrylamide or polyglycidylmethacrylate-dimethylacrylamide (PGMA-DMAA) block copolymer), water-soluble nylon, polyvinyl alcohol, polyvinyl pyrrolidone, or the like.

When the hydrophilic material is wetted (absorbs water), it provides lubrication to reduce friction (sliding resistance) between the guide wire 1 and the inner wall of the catheter that is used with the guide wire 1. The slidability of the guide wire 1 is increased to improve the operability of the guide wire 1 in the catheter.

Figure 3:
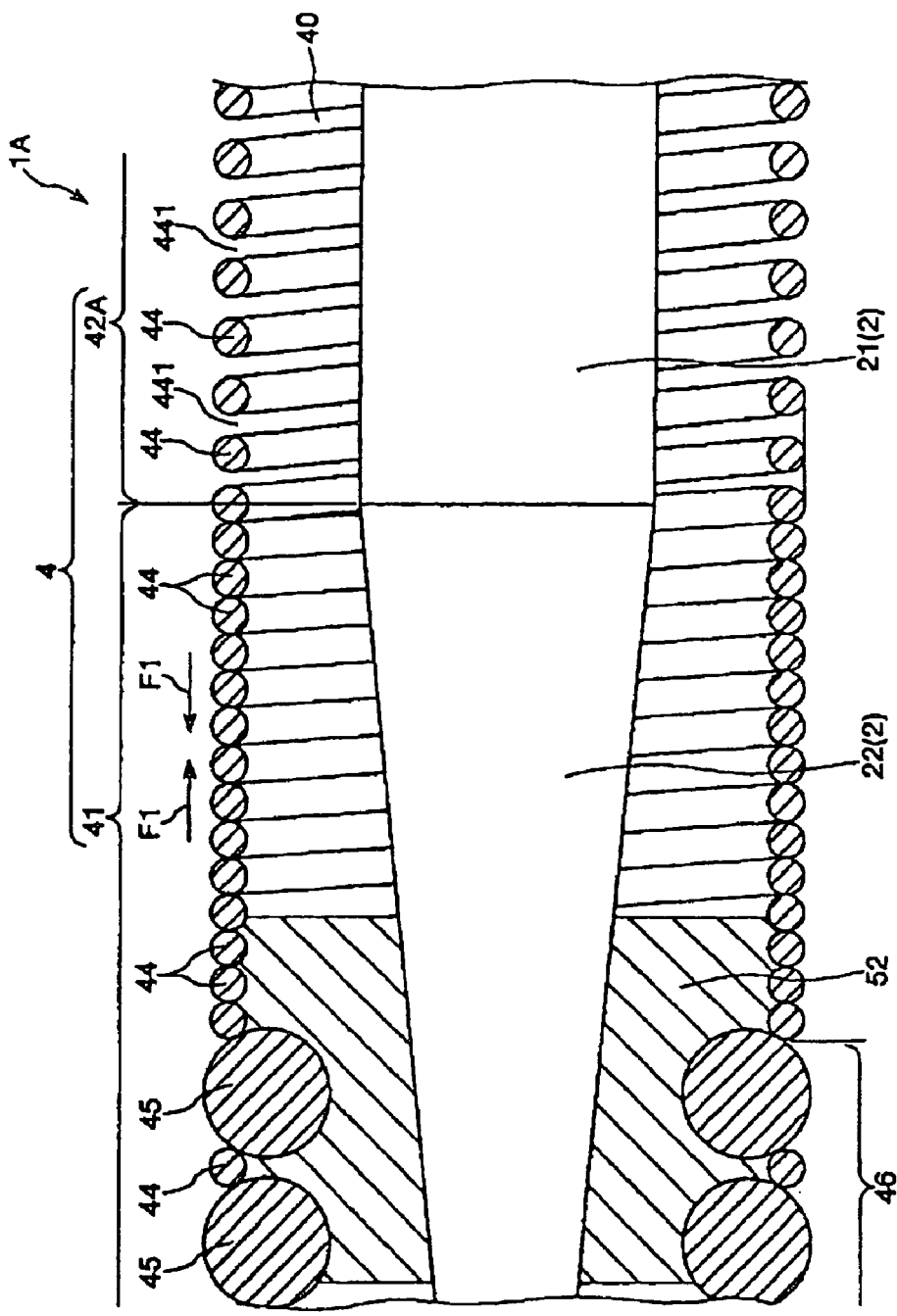
FIG. 3 is an enlarged detailed view showing a tapered portion of a guide wire according to a second embodiment.

FIG. 3 is an enlarged detailed view showing a portion of a guide wire (a portion similar to that illustrated in FIG. 2) according to a second embodiment. The description which follows primarily described differences between the guide wire according to the second embodiment relative to the embodiment of the guide wire described above. Features associated with the second embodiment of the guide wire that are similar to those associated with the first embodiment are identified by reference numerals similar to those used in the first embodiment, and a detailed description of such features will not be repeated.

The second embodiment of the guide wire shown in FIG. 3 is similar to the first embodiment, except that the second coil portion is formed differently. In the second coil portion 42A of the guide wire 1A shown in FIG. 3, adjacent turns of the wire 44 are spaced from each other with gaps 441 between the adjacent turns of the wire 44. In the second coil portion 42A, no initial tensile forces F2 are developed, i.e., initial tensile forces F2 are nil.

When the guide wire 1A is inserted into a catheter or a living body, forces that the guide wire 1A receives from its distal end are reduced by the gaps 441 of the second coil portion 42A, so that adjacent turns of the wire 44 of the first coil portion 41 described in the first embodiment are further prevented from riding onto each other. Therefore, the gaps 441 function as a damping mechanism or damping means for reducing the forces that the guide wire 1A (proximal portion of the guide wire 1A) receives from its distal end.

The pitch of the distal end portion of the second coil portion 42A (i.e., the center-to-center distance between adjacent windings of the second coil portion 42A) is reduced toward the distal end thereof to thereby distribute stresses between the first coil portion 41 and the second coil portion 42A.

While the guide wires according to the illustrated embodiments have been described above, the guide wire is not necessarily limited in this regard. Components of the guide wires may be replaced with other features and components performing the same or substantially similar functions. Additionally, features may be added to the guide wire.

By way of example, the embodiments of the guide wire described above include a coil formed of wires possessing a circular cross-sectional shape. However, the wires are not limited to the circular cross-sectional shape, but may be of an elliptical cross-sectional shape, a quadrangular (particularly rectangular) cross-sectional shape, or others.

The principles, preferred embodiments and other disclosed aspects have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A guide wire comprising:
    a wire body having a tapered portion disposed on a distal end portion of the wire body, the tapered portion of the wire body possessing an outside diameter that is progressively reduced toward a distal end of the tapered portion;
    a coil comprising at least one helically formed wire, the at least one helically formed wire comprising a first coil portion covering an outer circumferential surface of said tapered portion and a second coil portion disposed adjacent to a proximal end of said first coil portion and covering an outer circumferential surface of a portion of said wire body which is closer to a proximal end of the wire body than said tapered portion; and
    wherein adjacent turns of the at least one wire of said first coil portion are in contact with each other, adjacent turns of the at least one wire of said second coil portion are in contact with each other, and initial tensile forces which push the adjacent turns of the at least one wire in the first coil portion against each other axially of the wire body in a free state are greater than the initial tensile forces in the second coil portion in the free state.

2. The guide wire according to claim 1, wherein said portion of said wire body which is closer to the proximal end of the wire body than said tapered portion possesses an outside diameter that is constant along a longitudinal direction of the wire body.

3. The guide wire according to claim 2, wherein said at least one wire in the first coil portion possesses a wire diameter which is the same as the wire diameter of the at least one wire in said second coil portion.

4. The guide wire according to claim 1, wherein said first coil portion has an outside diameter which is the same as the outside diameter of said second coil portion.

5. The guide wire according to claim 1, wherein said first coil portion has an inside diameter which is the same as the inside diameter of said second coil portion.

6. The guide wire according to claim 1, wherein said at least one wire is a single wire so that said first coil portion and said second coil portion are made of the same material.

7. The guide wire according to claim 1, comprising:
    a plurality of spaced apart fixing materials which fix said coil to said wire body at a plurality of spaced apart locations;
    wherein each of said plurality of fixing materials is disposed at a position other than a boundary between said first coil portion and said second coil portion.

8. The guide wire according to claim 1, wherein the first coil portion comprises an angiographic portion.

9. The guide wire according to claim 8, wherein said at least one wire forming the coil comprises a first wire and a second wire, the first wire comprising the second coil portion and a portion of the first coil portion, the second wire forming the angiographic portion of said first coil portion, and the second wire possessing a wire diameter greater than the wire diameter of the first wire.

10. The guide wire according to claim 9, wherein said second wire meshes with said first wire at a boundary between a distal end of the first wire and a proximal end of the second wire.

11. The guide wire according to claim 1, wherein said at least one wire in the first coil portion possesses a wire diameter which is the same as the wire diameter of the at least one wire in said second coil portion.

12. The guide wire according to claim 1, wherein said wire body also comprises a first constant outer diameter portion on the distal end of the tapered portion of the wire body and a second constant outer diameter portion on the proximal end of the tapered portion of the wire body, the first constant outer diameter portion having a proximal end connected to the distal end of the tapered portion, the second constant outer diameter portion having a distal end connected to the proximal end of the tapered portion.

13. The guide wire according to claim 1, wherein a proximal end portion of the first coil portion comprises gradually reduced initial tensile forces.

14. A guide wire comprising:
    a wire body having a tapered portion disposed on a distal end portion of the wire body, the tapered portion of the wire body possessing an outside diameter that is progressively reduced toward a distal end of the tapered portion;

a coil disposed in covering relation to an outer circumferential surface of a distal end portion of said wire body, said coil being comprised of at least one helically formed wire;

wherein said coil comprises a first coil portion covering an outer circumferential surface of said tapered portion, and a second coil portion covering an outer circumferential surface of a portion of said wire body other than said tapered portion; and adjacent turns of the at least one wire of said first coil portion are in contact with each other, adjacent turns of the at least one wire of said second coil portion are in contact with each other, and initial tensile forces which push the adjacent turns of the at least one wire in the first coil portion against each other axially of the wire body in a free state are greater than the initial tensile forces in the second coil portion in the free state.

15. The guide wire according to claim 14, wherein said at least one wire includes a first wire and a second wire, the first wire comprising the first coil portion and the second coil portion, and the second wire possessing a wire diameter greater than a wire diameter of the first wire.

16. The guide wire according to claim 14, wherein the first coil portion is disposed distally of the second coil portion, and a proximal end portion of the first coil portion comprises gradually reduced initial tensile forces.

* * * * *